US010232141B2

(12) United States Patent
Christian et al.

(10) Patent No.: US 10,232,141 B2
(45) Date of Patent: *Mar. 19, 2019

(54) MICRO-CUTTING SYSTEMS FOR FORMING CUTS IN PRODUCTS

(71) Applicant: SCIENTIA VASCULAR, LLC, West Valley City, UT (US)

(72) Inventors: Jeff Christian, Morgan Hill, CA (US); Ryan Christian, Gilroy, CA (US); James A. Gasbarro, Pittsburgh, PA (US); Scott K. Boehmke, Wexford, PA (US); John Lippert, Park City, UT (US)

(73) Assignee: Scientia Vascular, LLC, West Valley City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/465,399

(22) Filed: Mar. 21, 2017

(65) Prior Publication Data

US 2017/0189643 A1 Jul. 6, 2017

Related U.S. Application Data

(63) Continuation of application No. 13/901,375, filed on May 23, 2013, now Pat. No. 9,662,798, which is a
(Continued)

(51) Int. Cl.
*A61M 25/00* (2006.01)
*B26D 5/00* (2006.01)
(Continued)

(52) U.S. Cl.
CPC ........ *A61M 25/0015* (2013.01); *A61M 25/09* (2013.01); *B26D 1/24* (2013.01);
(Continued)

(58) Field of Classification Search
CPC .............. A61M 25/0015; A61M 25/09; A61M 2025/09108; B26D 5/34; B26D 7/06;
(Continued)

(56) References Cited

U.S. PATENT DOCUMENTS 2,022,065 A 11/1935 Wappler
2,187,299 A 1/1940 Burkhardt
(Continued)

FOREIGN PATENT DOCUMENTS

AU 7230740 11/1997
AU 733966 5/2001
(Continued)

OTHER PUBLICATIONS

Supplementary European Search Report for EP10759515.9 dated Sep. 25, 2012.
(Continued)

*Primary Examiner* — Ghassem Alie
(74) *Attorney, Agent, or Firm* — Workman Nydegger

(57) ABSTRACT

This disclosure describes a micro-cutting machine for forming cuts in catheters, guidewires, and similar products. The micro-cutting machine can directly control the dimensions of the resultant beams being cut into these types of products, and can also capture images of each cut for feedback control and accuracy verification. The micro-cutting machine has two cutting blades each with cutting edges aligned with a vertical axis. Motors operate to move the cutting blades in a direction perpendicular to the longitudinal axis of the stock material being cut to form a pair of opposing grooves in the stock material with each cut.

20 Claims, 6 Drawing Sheets

Related U.S. Application Data continuation of application No. 12/633,727, filed on Dec. 8, 2009, now Pat. No. 8,468,919.

(60) Provisional application No. 61/166,480, filed on Apr. 3, 2009, provisional application No. 61/120,703, filed on Dec. 8, 2008.

(51) Int. Cl.
| | |
|---|---|
| A61M 25/09 | (2006.01) |
| B26F 1/00 | (2006.01) |
| B26D 5/20 | (2006.01) |
| B26D 5/34 | (2006.01) |
| B26D 7/06 | (2006.01) |
| B26D 1/24 | (2006.01) |

(52) U.S. Cl.
CPC .............. B26D 5/007 (2013.01); B26D 5/20 (2013.01); B26D 5/34 (2013.01); B26D 7/06 (2013.01); B26D 7/0683 (2013.01); B26F 1/0053 (2013.01); B26F 1/0061 (2013.01); B26F 1/0076 (2013.01); *A61M 2025/09108* (2013.01); *Y10T 83/0448* (2015.04); *Y10T 83/051* (2015.04); *Y10T 83/145* (2015.04); *Y10T 83/173* (2015.04); *Y10T 83/4458* (2015.04); *Y10T 83/4463* (2015.04); *Y10T 83/828* (2015.04); *Y10T 83/8878* (2015.04)

(58) Field of Classification Search
CPC ........ B26D 7/0683; B26D 5/20; B26D 5/007; B25F 1/0061; Y10T 83/4458; Y10T 83/051; Y10T 83/828; Y10T 83/0448; Y10T 83/145; Y10T 83/8878; B26F 1/0053
USPC ...... 83/36, 209, 73, 83, 211, 520, 821, 76.6, 83/76, 13, 62, 62.1, 310, 23, 578, 614, 83/485; 451/18, 15, 8, 9, 41, 12, 13.01; 700/101, 99, 100, 121; 438/16, 113, 14, 438/33
See application file for complete search history.

(56) References Cited

U.S. PATENT DOCUMENTS

| | | | |
|---|---|---|---|
| 3,572,334 A | 3/1971 | Petterson |
| 3,612,058 A | 10/1971 | Ackerman |
| 3,709,271 A | 1/1973 | Flory |
| 3,920,058 A | 11/1975 | Walker |
| 4,163,406 A | 8/1979 | Crawford |
| 4,239,069 A | 12/1980 | Zimmerman |
| 4,416,312 A | 11/1983 | Ostberg |
| 4,688,540 A | 8/1987 | Ono |
| 4,719,924 A | 1/1988 | Crittenden |
| 4,846,186 A | 7/1989 | Box |
| 4,895,168 A | 1/1990 | Machek |
| 4,989,608 A | 2/1991 | Ratner |
| 5,047,045 A | 9/1991 | Arney et al. |
| 5,069,217 A | 12/1991 | Fleischhacker |
| 5,084,022 A | 1/1992 | Claude |
| 5,095,915 A | 3/1992 | Angelson |
| 5,102,390 A | 4/1992 | Crittenden et al. |
| 5,147,317 A | 9/1992 | Shank |
| 5,154,725 A | 10/1992 | Leopold |
| 5,174,302 A | 12/1992 | Palmer |
| 5,315,996 A | 5/1994 | Lundquist |
| 5,326,374 A | 7/1994 | Ilbawi et al. |
| 5,372,587 A | 12/1994 | Hammerslag |
| 5,382,259 A | 1/1995 | Phelps |
| 5,385,152 A | 1/1995 | Abele |
| 5,437,288 A | 8/1995 | Schwartz |
| 5,441,483 A | 8/1995 | Avitall |
| 5,506,682 A | 4/1996 | Pryor |
| 5,507,751 A | 4/1996 | Goode et al. |
| 5,551,444 A | 9/1996 | Finlayson |
| 5,554,114 A | 9/1996 | Wallace et al. |
| 5,573,520 A | 11/1996 | Schwartz |
| 5,673,707 A | 10/1997 | Chandrasekaran |
| 5,676,659 A | 10/1997 | McGurk |
| 5,685,868 A | 11/1997 | Lundquist |
| 5,690,120 A | 11/1997 | Jacobsen |
| 5,741,429 A | 4/1998 | Donadio |
| 5,746,701 A | 5/1998 | Noone |
| 5,792,154 A | 8/1998 | Doan |
| 5,800,454 A | 9/1998 | Jacobsen |
| 5,833,631 A | 11/1998 | Nguyen |
| 5,860,963 A | 1/1999 | Azam |
| 5,876,356 A | 3/1999 | Viera et al. |
| 5,911,715 A | 6/1999 | Berg |
| 5,911,717 A | 6/1999 | Jacobsen |
| 5,916,194 A | 6/1999 | Jacobsen |
| 5,931,830 A | 8/1999 | Jacobsen |
| 6,004,279 A | 12/1999 | Crowley |
| 6,014,919 A | 1/2000 | Jacobsen |
| 6,017,319 A | 1/2000 | Jacobsen |
| 6,022,343 A | 2/2000 | Johnson et al. |
| 6,022,369 A | 2/2000 | Jacobsen |
| 6,027,863 A | 2/2000 | Donadis |
| 6,033,288 A | 3/2000 | Weisshaus |
| 6,033,394 A | 3/2000 | Vidlund |
| 6,056,702 A | 5/2000 | Lorenzo |
| 6,063,101 A | 5/2000 | Jacobsen |
| 6,132,389 A | 10/2000 | Cornish |
| 6,139,511 A | 10/2000 | Huter |
| 6,168,570 B1 | 1/2001 | Ferrera |
| 6,179,828 B1 | 1/2001 | Mottola |
| 6,183,410 B1 | 2/2001 | Jacobsen |
| 6,214,042 B1 | 4/2001 | Jacobsen |
| 6,228,073 B1 | 5/2001 | Noone |
| 6,245,030 B1 | 6/2001 | Dubois |
| 6,251,086 B1 | 6/2001 | Cornelius |
| 6,260,458 B1 | 7/2001 | Jacobsen |
| 6,261,246 B1 | 7/2001 | Pantages et al. |
| 6,302,870 B1 | 10/2001 | Jacobsen |
| 6,306,105 B1 | 10/2001 | Rooney |
| 6,346,091 B1 | 2/2002 | Jacobsen |
| 6,356,791 B1 | 3/2002 | Westlund |
| 6,402,706 B2 | 6/2002 | Richardson et al. |
| 6,428,489 B1 | 8/2002 | Jacobsen |
| 6,431,039 B1 | 8/2002 | Jacobsen |
| 6,436,056 B1 | 8/2002 | Wang et al. |
| 6,440,088 B1 | 8/2002 | Jacobsen |
| 6,458,867 B1 | 10/2002 | Wang et al. |
| 6,464,651 B1 | 10/2002 | Hiejima et al. |
| 6,492,615 B1 | 12/2002 | Flanagan |
| 6,494,894 B2 | 12/2002 | Mirarchi |
| 6,527,732 B1 | 3/2003 | Strauss |
| 6,527,746 B1 | 3/2003 | Oslund |
| 6,553,880 B2 | 4/2003 | Jacobsen |
| 6,554,820 B1 | 4/2003 | Wendlandt |
| 6,558,355 B1 | 5/2003 | Metzger |
| 6,579,246 B2 | 6/2003 | Jacobsen |
| 6,602,207 B1 | 8/2003 | Mam |
| 6,606,985 B2 | 8/2003 | Negishi |
| 6,610,046 B1 | 8/2003 | Usami et al. |
| 6,652,508 B2 | 11/2003 | Griffin |
| 6,671,560 B2 | 12/2003 | Westlund |
| 6,766,720 B1 | 7/2004 | Jacobsen |
| 6,805,676 B2 | 10/2004 | Klint |
| RE39,018 E | 3/2006 | Azuma |
| 7,097,624 B2 | 8/2006 | Campion |
| 7,110,910 B1 | 9/2006 | Deffenbaugh |
| 7,276,062 B2 | 10/2007 | McDaniel et al. |
| 7,494,474 B2 | 2/2009 | Richardson et al. |
| 7,621,880 B2 | 11/2009 | Ryan |
| 7,637,875 B2 | 12/2009 | Itou |
| 7,641,622 B2 | 1/2010 | Satou |
| 7,670,302 B2 | 3/2010 | Griffin |
| 7,699,792 B2 | 4/2010 | Hofmann |
| 7,722,545 B2 | 5/2010 | Bertsch |
| 7,722,552 B2 | 5/2010 | Aimi |
| 7,744,545 B2 | 6/2010 | Aimi |

(56) References Cited

U.S. PATENT DOCUMENTS

| | | |
|---|---|---|
| 7,747,314 B2 | 6/2010 | Parins |
| 7,753,859 B2 | 7/2010 | Kinoshita |
| 7,766,896 B2 | 8/2010 | Volk |
| 7,785,273 B2 | 8/2010 | Eskuri |
| 7,789,839 B2 | 9/2010 | Lupton |
| 7,806,837 B2 | 10/2010 | Rasmussen |
| 7,878,984 B2 | 2/2011 | Davis |
| 7,883,474 B1 | 2/2011 | Mirigian |
| 7,914,467 B2 | 3/2011 | Layman et al. |
| 7,942,832 B2 | 5/2011 | Kanuka |
| 7,989,042 B2 | 8/2011 | Obara et al. |
| 8,043,314 B2 | 10/2011 | Noriega et al. |
| 8,048,004 B2 | 11/2011 | Davis et al. |
| 8,105,246 B2 | 1/2012 | Voeller |
| 8,128,579 B2 | 3/2012 | Chen |
| 8,128,580 B2 | 3/2012 | Fujimagari |
| 8,137,293 B2 | 3/2012 | Zhou |
| 8,167,821 B2 | 5/2012 | Sharrow et al. |
| 8,292,828 B2 | 10/2012 | Uihlein |
| 8,357,140 B2 | 1/2013 | Majercak |
| 8,377,056 B2 | 2/2013 | Oyola et al. |
| 8,409,114 B2 | 4/2013 | Parins |
| 8,444,577 B2 | 5/2013 | Bunch |
| 8,454,535 B2 | 6/2013 | Majercak |
| 8,460,213 B2 | 6/2013 | Northrop |
| 8,468,919 B2 | 6/2013 | Christian |
| 8,500,658 B2 | 8/2013 | Boyle |
| 8,517,959 B2 | 8/2013 | Kurosawa |
| 8,535,243 B2 | 9/2013 | Shireman |
| 8,540,648 B2 | 9/2013 | Uihlein |
| 8,551,020 B2 | 10/2013 | Chen et al. |
| 8,551,021 B2 | 10/2013 | Voeller |
| 8,622,931 B2 | 1/2014 | Teague |
| 8,622,933 B2 | 1/2014 | Maki |
| 8,795,202 B2 | 8/2014 | Northrop |
| 8,795,254 B2 | 8/2014 | Layman |
| 8,821,477 B2 | 9/2014 | Northrop |
| 8,870,790 B2 | 10/2014 | Jacobsen |
| 8,900,163 B2 | 12/2014 | Jacobsen |
| 8,915,865 B2 | 12/2014 | Jacobsen et al. |
| 8,932,235 B2 | 1/2015 | Jacobsen |
| 8,936,558 B2 | 1/2015 | Jacobsen |
| 8,939,916 B2 | 1/2015 | Jacobsen |
| 9,067,332 B2 | 6/2015 | Lippert |
| 9,067,333 B2 | 6/2015 | Lippert |
| 9,072,873 B2 | 7/2015 | Lipped |
| 9,072,874 B2 | 7/2015 | Northrop |
| 9,364,589 B2 | 6/2016 | Cage |
| 9,623,212 B2 | 4/2017 | Tano |
| 9,662,798 B2 | 5/2017 | Christian |
| 9,700,702 B2 | 7/2017 | Tano |
| 2002/0019599 A1 | 2/2002 | Rooney |
| 2002/0049392 A1 | 4/2002 | DeMello |
| 2002/0082524 A1 | 6/2002 | Anderson |
| 2003/0023190 A1 | 1/2003 | Cox |
| 2003/0069522 A1 | 4/2003 | Jacobsen |
| 2003/0093059 A1 | 5/2003 | Griffin et al. |
| 2004/0054349 A1 | 3/2004 | Brightbill |
| 2004/0087933 A1 | 5/2004 | Lee |
| 2004/0102719 A1 | 5/2004 | Keith et al. |
| 2004/0111044 A1 | 6/2004 | Davis |
| 2004/0167440 A1 | 8/2004 | Sharrow et al. |
| 2004/0181174 A2 | 9/2004 | Davis |
| 2004/0186485 A1 | 9/2004 | Kear |
| 2004/0193140 A1 | 9/2004 | Griffin |
| 2004/0254450 A1 | 12/2004 | Griffin et al. |
| 2005/0054953 A1 | 3/2005 | Ryan |
| 2005/0124976 A1 | 6/2005 | Devens |
| 2005/0216049 A1 | 9/2005 | Jones et al. |
| 2005/0274384 A1 | 12/2005 | Tran et al. |
| 2006/0041186 A1 | 2/2006 | Vancaillie |
| 2006/0089618 A1 | 4/2006 | McFerran |
| 2006/0112802 A1 | 6/2006 | Fujinami |
| 2006/0121218 A1 | 6/2006 | Obara et al. |
| 2006/0241519 A1 | 10/2006 | Hojeibane et al. |
| 2007/0010786 A1 | 1/2007 | Casey et al. |
| 2007/0100285 A1 | 5/2007 | Griffin |
| 2007/0112331 A1 | 5/2007 | Weber et al. |
| 2007/0135763 A1 | 6/2007 | Musbach |
| 2007/0142893 A1 | 6/2007 | Buiser et al. |
| 2007/0167876 A1 | 7/2007 | Euteneuer et al. |
| 2007/0185415 A1 | 8/2007 | Ressemann et al. |
| 2007/0221230 A1 | 9/2007 | Thompson |
| 2007/0250036 A1 | 10/2007 | Volk |
| 2007/0287955 A1 | 12/2007 | Layman et al. |
| 2008/0021347 A1 | 1/2008 | Jacobsen et al. |
| 2008/0021404 A1 | 1/2008 | Jacobsen et al. |
| 2008/0064989 A1 | 3/2008 | Chen et al. |
| 2008/0077049 A1 | 3/2008 | Hirshman |
| 2008/0086854 A1 | 4/2008 | Boyd |
| 2008/0097247 A1 | 4/2008 | Eskuri |
| 2008/0097248 A1 | 4/2008 | Munoz |
| 2008/0119869 A1 | 5/2008 | Teague et al. |
| 2008/0125674 A1 | 5/2008 | Bilecen et al. |
| 2008/0147170 A1 | 6/2008 | Vrba |
| 2008/0188928 A1 | 8/2008 | Salahieh |
| 2008/0200839 A1 | 8/2008 | Bunch et al. |
| 2008/0262474 A1 | 10/2008 | Northrop |
| 2008/0269641 A1 | 10/2008 | O'Shaughnessy et al. |
| 2008/0319525 A1 | 12/2008 | Tieu |
| 2009/0036833 A1 | 2/2009 | Parins |
| 2009/0043283 A1 | 2/2009 | Turnlund |
| 2009/0043372 A1 | 2/2009 | Northrop et al. |
| 2009/0118675 A1 | 5/2009 | Czyscon et al. |
| 2009/0177119 A1 | 7/2009 | Heidner |
| 2009/0318892 A1 | 12/2009 | Aboytes et al. |
| 2010/0063479 A1 | 3/2010 | Merddan |
| 2010/0114017 A1 | 5/2010 | Lenker et al. |
| 2010/0114302 A1 | 5/2010 | Tzafriri et al. |
| 2010/0256528 A1 | 10/2010 | Lippert |
| 2010/0256601 A1 | 10/2010 | Lippert |
| 2010/0256602 A1 | 10/2010 | Lippert |
| 2010/0256603 A1 | 10/2010 | Lippert |
| 2010/0256604 A1 | 10/2010 | Lippert |
| 2010/0256606 A1 | 10/2010 | Lippert et al. |
| 2011/0022003 A1 | 1/2011 | Tekulve |
| 2011/0160680 A1 | 6/2011 | Cage et al. |
| 2012/0065623 A1 | 3/2012 | Nelson, III |
| 2012/0158034 A1 | 6/2012 | Wilson |
| 2012/0209073 A1 | 8/2012 | McWeeney et al. |
| 2012/0239074 A1 | 9/2012 | Aboytes et al. |
| 2012/0271397 A1 | 10/2012 | Muzslay et al. |
| 2013/0018359 A1 | 1/2013 | Coyle |
| 2013/0096553 A1 | 4/2013 | Hill et al. |
| 2013/0110000 A1 | 5/2013 | Tully |
| 2013/0255456 A1 | 10/2013 | Christian et al. |
| 2014/0094787 A1 | 4/2014 | Reynolds |
| 2014/0187983 A1 | 7/2014 | Anderson |
| 2014/0257363 A1 | 9/2014 | Lippert |
| 2015/0011964 A1 | 1/2015 | Abner |
| 2015/0190614 A1 | 7/2015 | Uihlein |
| 2015/0238734 A1 | 8/2015 | Kanazawa |
| 2015/0290432 A1 | 10/2015 | Mathews |
| 2015/0305710 A1 | 10/2015 | Koninklijke |
| 2016/0008585 A1 | 1/2016 | Tano |
| 2016/0089128 A1 | 3/2016 | Weber |
| 2016/0113793 A1 | 4/2016 | Nishigishi |
| 2016/0135827 A1 | 5/2016 | Elsesser |
| 2016/0199620 A1 | 7/2016 | Pokorney |
| 2016/0235337 A1 | 8/2016 | Govari |
| 2016/0361520 A1 | 12/2016 | Braun |
| 2016/0375226 A1 | 12/2016 | Nabeshima |
| 2017/0189643 A1 | 7/2017 | Christian |
| 2018/0015261 A1 | 1/2018 | Lippert |
| 2018/0015262 A1 | 1/2018 | Lippert |
| 2018/0015263 A1 | 1/2018 | Lippert |
| 2018/0071496 A1 | 3/2018 | Snyder |
| 2018/0177517 A1 | 6/2018 | Lippert |

FOREIGN PATENT DOCUMENTS

| | | |
|---|---|---|
| AU | 774559 | 7/2004 |
| AU | 2008229892 | 10/2008 |
| BR | 9709363 | 1/2000 |

(56) References Cited

FOREIGN PATENT DOCUMENTS

| | | |
|---|---|---|
| BR | 9712829 | 1/2000 |
| CA | 2266685 | 5/2006 |
| CA | 2255781 | 3/2007 |
| CA | 2395149 | 12/2008 |
| CN | 1230914 | 10/1999 |
| CN | 1324285 | 11/2001 |
| CN | 1422673 | 6/2003 |
| CN | 1518428 | 8/2004 |
| CN | 1781684 | 6/2006 |
| CN | 101001660 | 7/2007 |
| CN | 101304778 | 11/2008 |
| DE | 60036882 | 7/2008 |
| DE | 69738235 | 7/2008 |
| EP | 0934141 | 11/2005 |
| EP | 0921754 | 10/2007 |
| EP | 1239901 | 10/2007 |
| EP | 1940498 | 7/2008 |
| ES | 2293660 | 3/2008 |
| JP | 59102509 S | 6/1984 |
| JP | 07-008560 | 1/1995 |
| JP | 08-308934 | 11/1996 |
| JP | 11294497 H | 10/1999 |
| JP | 2000116787 | 4/2000 |
| JP | 2000511094 | 8/2000 |
| JP | 2000343313 | 12/2000 |
| JP | 2001500808 | 1/2001 |
| JP | 2002543896 | 12/2002 |
| JP | 2003011117 | 1/2003 |
| JP | 200425340 | 5/2004 |
| JP | 2004329552 | 11/2004 |
| JP | 2004535233 | 11/2004 |
| JP | 2005533594 | 11/2005 |
| JP | 2007313638 | 12/2007 |
| JP | 2008536639 | 11/2008 |
| JP | 2010535588 | 11/2010 |
| JP | 4805208 | 11/2011 |
| JP | 4845313 | 12/2011 |
| KR | 20000015896 | 3/2000 |
| KR | 20000036139 | 6/2000 |
| TW | 412468 | 11/2000 |
| WO | 1994006503 | 3/1994 |
| WO | 2004011076 | 2/2004 |
| WO | 2006113863 | 10/2006 |
| WO | 2007050718 | 5/2007 |
| WO | 2009020961 | 2/2009 |
| WO | 2009020962 | 2/2009 |
| WO | 2010077692 | 7/2010 |
| WO | 2010115163 | 10/2010 |
| WO | 2014138580 | 9/2014 |
| WO | 2016047499 | 3/2016 |
| WO | 2016117238 | 7/2016 |
| WO | 2016136609 | 9/2016 |
| WO | 2016152194 | 9/2016 |
| WO | 2016158671 | 10/2016 |

OTHER PUBLICATIONS

International Search Report for PCT/US2009/067217 dated Dec. 16, 2010.
International Search Report for PCT/US2010/029867 dated Jun. 1, 2010.
European Search Report for EP09836735 dated Nov. 7, 2012.
European Search Report for EP15197042 dated Apr. 11, 2016.
U.S. Appl. No. 12/753,858, May 10, 2011, Office Action.
U.S. Appl. No. 12/753,849, May 10, 2011, Office Action.
U.S. Appl. No. 12/753,855, Sep. 15, 2011, Office Action.
U.S. Appl. No. 12/753,849, Oct. 18, 2011, Office Action.
U.S. Appl. No. 12/753,858, Oct. 19, 2011, Final Office Action.
U.S. Appl. No. 12/753,836, Dec. 9, 2011, Office Action.
U.S. Appl. No. 12/753,831, Feb. 1, 2012, Office Action.
U.S. Appl. No. 12/753,839, Feb. 7, 2012, Office Action.
U.S. Appl. No. 12/753,855, Apr. 18, 2012, Final Office Action.
U.S. Appl. No. 12/753,836, May 1, 2012, Final Office Action.
U.S. Appl. No. 12/753,831, May 31, 2012, Final Office Action.
U.S. Appl. No. 12/753,839, May 31, 2012, Final Office Action.
U.S. Appl. No. 12/753,849, Jun. 6, 2012, Final Office Action.
U.S. Appl. No. 12/753,858, Jul. 18, 2012, Final Office Action.
U.S. Appl. No. 12/753,842, Aug. 1, 2012, Office Action.
U.S. Appl. No. 12/633,727, Oct. 16, 2012, Office Action.
U.S. Appl. No. 12/753,849, Jan. 3, 2013, Office Action.
U.S. Appl. No. 12/753,842, Jan. 9, 2013, Final Office Action.
U.S. Appl. No. 12/633,727, Feb. 28, 2013, Notice of Allowance.
U.S. Appl. No. 12/753,858, Mar. 29, 2013, Office Action.
U.S. Appl. No. 12/753,849, Oct. 9, 2013, Final Office Action.
U.S. Appl. No. 12/753,858, Jan. 17, 2014, Final Office Action.
U.S. Appl. No. 12/753,842, Jan. 29, 2014, Office Action.
U.S. Appl. No. 12/753,855, Feb. 28, 2014, Office Action.
U.S. Appl. No. 12/753,831, Mar. 21, 2014, Office Action.
U.S. Appl. No. 12/753,839, May 5, 2014, Office Action.
U.S. Appl. No. 12/753,849, May 27, 2014, Office Action.
U.S. Appl. No. 12/753,836, Jul. 31, 2014, Office Action.
U.S. Appl. No. 12/753,831, Aug. 29, 2014, Final Office Action.
U.S. Appl. No. 12/753,842, Sep. 4, 2014, Final Office Action.
U.S. Appl. No. 12/753,858, Sep. 4, 2014, Office Action.
U.S. Appl. No. 12/753,858, Nov. 4, 2014, Interview Summary.
U.S. Appl. No. 12/753,849, Dec. 5, 2014, Interview Summary.
U.S. Appl. No. 12/753,842, Dec. 29, 2014, Notice of Allowance.
U.S. Appl. No. 12/753,836, Jan. 9, 2015, Final Office Action.
U.S. Appl. No. 12/753,855, Jan. 13, 2015, Final Office Action.
U.S. Appl. No. 12/753,849, Feb. 2, 2015, Notice of Allowance.
U.S. Appl. No. 12/753,842, Mar. 5, 2015, Notice of Allowance.
U.S. Appl. No. 12/753,831, Apr. 14, 2015, Notice of Allowance.
U.S. Appl. No. 12/753,849, Apr. 30, 2015, Notice of Allowance.
U.S. Appl. No. 12/753,855, May 21, 2015, Office Action.
U.S. Appl. No. 12/753,858, May 28, 2015, Final Office Action.
U.S. Appl. No. 12/753,836, Jun. 26, 2015, Office Action.
U.S. Appl. No. 13/901,375, Dec. 10, 2015, Office Action.
U.S. Appl. No. 12/753,858, Dec. 30, 2015, Office Action.
U.S. Appl. No. 12/753,836, Feb. 17, 2016, Final Office Action.
U.S. Appl. No. 12/753,855, May 5, 2016, Office Action.
U.S. Appl. No. 13/901,375, Aug. 1, 2016, Office Action.
U.S. Appl. No. 12/753,858, Oct. 24, 2016, Office Action.
U.S. Appl. No. 12/753,855, Nov. 30, 2016, Notice of Allowance.
U.S. Appl. No. 12/753,836, Dec. 23, 2016, Office Action.
U.S. Appl. No. 13/901,375, Dec. 27, 2016, Notice of Allowance.
U.S. Appl. No. 12/753,858, Mar. 27, 2017, Office Action.
U.S. Appl. No. 12/753,836, Jul. 14, 2017, Final Office Action.
U.S. Appl. No. 12/753,858, Oct. 20, 2017, Final Office Action.
U.S. Appl. No. 12/753,836, Nov. 24, 2017, Notice of Allowance.
European Search Report for application No. 17184064.8 dated Jan. 5, 2018.
Canadian Office Action for CA2757655 dated Jan. 2, 2018.
International Search Report and Written Opinion for application No. PCT/US17/41299 dated Oct. 2, 2017.
International Search Report and Written Opinion for application No. PCT/US17/41301 dated Oct. 2, 2017.
International Search Report and Written Opinion for application No. PCT/US17/41305 dated Oct. 2, 2017.
U.S. Appl. No. 15/917,255, filed Mar. 9, 2018, Lippert.
U.S. Appl. No. 12/753,858, Mar. 13, 2018, Office Action.
Supplementary Partial European Search Report for EP14760849 dated Oct. 11, 2016.
International Search Report and Written Opinion for PCT/US2014/021742 dated Aug. 27, 2014.
International Search Report and Written Opinion for application PCT/US2017/050802 dated Nov. 7, 2017.
International Search Report and Written Opinion for PCT/US2017/068056 dated Feb. 26, 2018.
International Search Report and Written Opinion for PCT/US2018/034723 dated Sep. 5, 2018.
International Search Report and Written Opinion for PCT/U52018/03478356 dated Aug. 14, 2018.
U.S. Appl. No. 12/753,858, filed Nov. 14, 2018, Final Office Action.
U.S. Appl. No. 14/199,675, filed Nov. 3, 2016, Office Action.
U.S. Appl. No. 14/199,675, filed May 18, 2017, Final Office Action.

(56) References Cited

OTHER PUBLICATIONS

U.S. Appl. No. 14/199,675, filed Sep. 6, 2017, Notice of Allowance.

FIG. 5A    FIG. 5B

MICRO-CUTTING SYSTEMS FOR FORMING CUTS IN PRODUCTS

CROSS-REFERENCE TO RELATED APPLICATIONS

The present application is a continuation of U.S. patent application Ser. No. 13/901,375, filed May 23, 2013, which is a continuation of U.S. patent application Ser. No. 12/633,727, filed Dec. 8, 2009, which claims the benefit of and priority to U.S. Provisional Patent Application Ser. No. 61/120,703, filed 8 Dec. 2008, and U.S. Provisional Patent Application Ser. No. 61/166,480, filed 3 Apr. 2009, each of which are herein incorporated by reference in their entirety.

BRIEF DESCRIPTION OF THE INVENTION

Micro-cutting machines for forming cuts in catheters, guidewires, and similar products, are disclosed, including a dual blade micro-cutting machine that can directly control the dimensions of the resultant beams being cut into the products, that can capture images of each cut for feedback control and accuracy verification, and that generally can cut any material (such as plastic) independent of the conductivity of the material.

BACKGROUND OF THE INVENTION

The medical field utilizes highly flexible and torquable catheters and guidewires to perform delicate procedures deep inside the human body. Endovascular procedures typically start at the groin where a catheter and guidewire are inserted into the femoral artery and navigated up to the heart, brain, or other anatomy as required. Once in place, the guidewire is removed so the catheter can be used for the delivery of drugs, stents, embolic devices to treat a variety of conditions, or other devices or agents. The catheter may be a balloon catheter used for therapy directly, either by itself or with a balloon expandable stent pre-loaded on it. A radiopaque dye is often injected into the catheter so that the vessels can be viewed intraprocedurally or in the case of a diagnostic procedure, the dye may be the primary or only agent delivered through the catheter.

Intravascular procedures, by definition, work in and with delicate anatomy, namely the vessels themselves, which are often also compromised by disease. Damage to the vessels is particularly critical to avoid. If blood in the vessels is allowed to "leak," direct damage can be caused to any tissue outside of the normal capillary approach contacted by the blood, and/or may result in a deadly problem of exsanguination or "bleed out". When treating an aneurysm, the control of the catheter tip is especially important. An aneurysm is a very fragile ballooned vessel wall which can easily be punctured if the guidewire or catheter is not precisely controlled.

The guidewires and catheters produced with current technology machines (as described in published patents) have limited functionality. An example of such a micro-cutting machine is disclosed in U.S. Pat. No. 6,014,919, issued to Jacobsen et al. on 18 Jan. 2000. Due to the single blade design and other aspects of these existing machines, the machines lack the precision necessary to control small (sub 0.002") features on a reliable basis. They also lack the ability to precisely control and verify larger features, which could affect the safety and/or performance of these devices. These machines are also only capable of working with electrically conductive stock material because the machines rely on the electrical conductivity of the stock material to determine the position of the stock relative to the cutting blade. Each cut made by the blade into the stock is based on the location of the electromagnetically sensed surface of the stock and the pre-programmed depth of the desired cut. Once a cut is made, the stock piece is rotated 180 degrees, the surface is sensed again, and another pre-programmed cut is made to a desired depth. As the cutting machine is incapable of determining the precise diameter (at the location of the cut) of the stock material being cut, each cut is made according to a preprogrammed depth regardless of that diameter. This is a problem because stock material is not always of a uniform shape and diameter—there are often imperfections along the length of stock that can affect both the roundness of the stock material and the diameter of the stock material at any particular location.

When the stock material is cut in the manner practiced by current cutting machines, a small beam of remaining material, of varying thickness, is formed by the sequential, opposing cuts. This beam is referred to as a resultant beam. If the diameter of the stock is thicker than anticipated at the location of the cuts, then the resultant beam will be thicker and therefore less flexible than desired. If the diameter of the stock is thinner than anticipated at the location of the cuts, then the resultant beam will be thinner and therefore weaker than desired. Thus, the critical dimension that governs both strength (safety) and flexibility (performance) is the width of the resultant beam, which in current micro-cutting machines is not controlled directly and is instead the result of two imprecise measurements—the measure of the relative distance between the blade and the stock material for the first cut and the measure of the relative distance between the blade and the stock material for the second cut. Any imperfection in the surface of the stock material, or inconsistency in the diameter of such material, is directly translated to the resultant beam. This is problematic in terms of both safety and performance of the final product, whether it is a guidewire, catheter or other device. It is especially critical when forming small dimension resultant beams relative to a larger dimension stock material, as an acceptable tolerance relative to the larger diameter of the stock material may be unacceptably large compared to the smaller dimension of the resultant beam. Existing technology is also unable to cut any kind of non-conductive material, such as plastic. The existing cutting machines rely upon electrical conductivity to sense the surface of the material being cut and then make the cuts.

It would therefore be advantageous to create a micro-cutting machine for machining catheters, guidewires and other devices that utilizes two blades to cut both sides simultaneously, that is able to directly control the width of resultant beams, and that is capable of micro-cutting non-conductive material, such as plastic. Such a machine would be faster, more predictable, and more versatile than current micro-cutting machines.

BRIEF DESCRIPTION OF THE SEVERAL VIEWS OF THE DRAWINGS

FIGS. 5A, 5B and 5C illustrate different views of a product cut in accordance with an embodiment.

DETAILED DESCRIPTION OF THE INVENTION

The herein disclosed micro-cutting machine utilizes a pair of micro-cutting blades or other cutting members to precisely cut into opposing sides of a cylindrical stock material. By cutting both sides simultaneously while tightly controlling the distance between the blades or cutting members, the disclosed micro-cutting machine is capable of producing high performance catheters, guidewires and related products for interventional medical procedures, as well as other devices for a variety of additional uses. While an embodiment has been designed primarily for cutting stock material into flexible and torquable medical guidewires and catheters, the disclosed micro-cutting machine can certainly be used for other applications, and may be appropriate for making precise micro-cuts into a wide variety of cylindrical materials or perhaps even other extruded stock materials which may have non-circular cross-sectional shapes. The micro-cutting machine will mostly be described in regard to cutting guidewires and catheters, but those skilled in the art will recognize the broader applicability of the embodiment.

Figure 1:
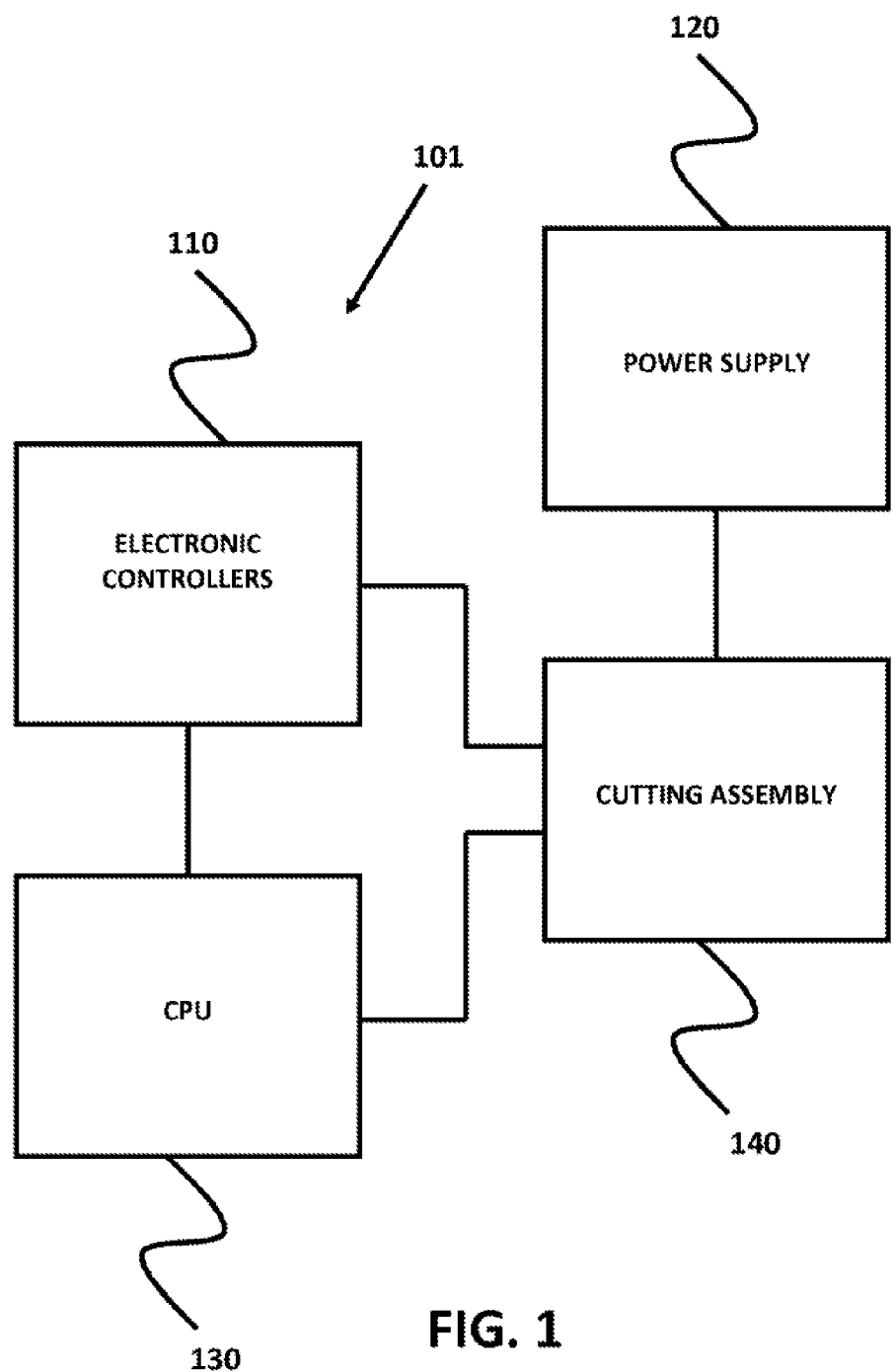
FIG. 1 illustrates a general overview of a micro-cutting machine in an embodiment.

FIG. 1 illustrates a general layout of the micro-cutting machine in accordance with an embodiment. Micro-cutting machine 101 includes cutting assembly 140, which generally has at least a pair of blades or cutting members and two or more stock material controllers, including feed and rotate motors, for precisely advancing and controlling the angle of the cylindrical stock material as it is cut and then preparing for a next cut. Cutting assembly 140 will be explained in much more detail below. Communicatively connected to cutting assembly 140 are electronic controllers 110 (which may be one or more electronic controllers, which are referred to as an electronic controller unit) for providing precise control signals to the cutting assembly 140 to control the position and speed of the blades and the position and angle of the stock material. The electronic controllers can also control the lights and a camera (an imaging system) for imaging the stock material before and after cuts and collecting data generated by the imaging system. A central processing unit 130 (such as a personal computer that includes a display, input and output systems, a storage system, etc., or some other type of CPU) receives user input, controls the electronic controllers 110 and the cutting assembly 140, and processes data generated by the imaging system to adjust the relative gap distance between the two blades. Alternatively, the CPU 130 could communicate directly with the imaging system and by-pass the electronic controllers 110. A power supply 120 supplies power to at least the cutting assembly 140, and possibly other components of the micro-cutting machine 101.

Figures 2A, 2B:
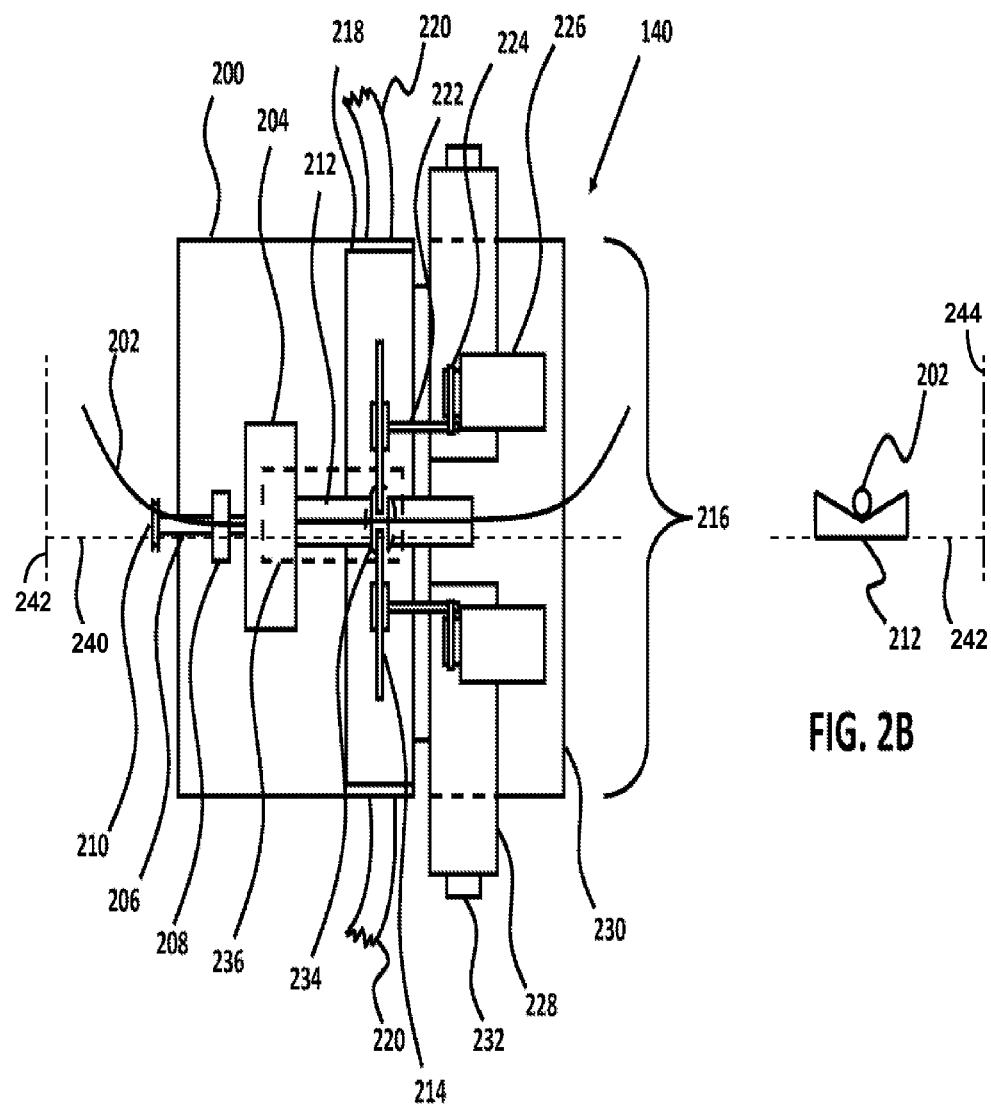
FIG. 2A illustrates a partially cut-away, plan view of a cutting assembly of the micro-cutting machine of FIG. 1 in an embodiment.
FIG. 2B illustrates a cross-sectional view of a piece of cylindrical stock material resting within a feed trough of the cutting assembly of FIG. 2A in an embodiment.

FIG. 2A illustrates a plan view of an embodiment of cutting assembly 140, which is mounted on a stationary frame assembly 200. The stock material 202 is fed into the cutting assembly 140 by the feed motor assembly 204, which can hold the stock material in a fixed position relative to the X-axis (shown in FIG. 2A as axis 240), the direction parallel to the spindle 206, and which can move the stock material along the X-axis by very small, controlled increments, so as to appropriately feed the stock material 202 into the cutting assembly 140, as further discussed below. The feed motor assembly 204 may comprise two feed motors (not separately shown), one for gripping the stock material 202 while it is being cut, as further described below, and one for moving the stock material 202 along the X-axis when the stock material 202 has been released by the first feed motor.

The stock material 202 shown in FIG. 2A is not illustrated as its actual size. The outer diameter of the stock material 202 can be 0.030 inches or less, or about 3 French on the French catheter scale, where a French is equal to three times the outer diameter of the stock material 202 measured in millimeters. Converting to inches, 3 French is equal to 0.039 inches, 4 French is equal to 0.053 inches, 5 French is equal to 0.066 inches, 6 French is equal to 0.079 inches, etc. Accordingly, based on the relative size of the cutting assembly shown in FIG. 2A, even a length of 6 French stock material 202 would be so small as to be almost impossible to see clearly, so the stock material 202 illustrated in FIG. 2A is much larger than its actual size for purposes of this illustration only.

The feed motor assembly 204 is mounted on a spindle 206 that is supported within the bearings of a bracket 208 mounted to the stationary frame assembly 200. A pulley 210 mounted to the spindle 206 is driven by a belt (not shown) that is, in turn, connected to another pulley (not shown) below the pulley 210, which is connected to a rotational motor (not shown) mounted within the stationary frame assembly 200. The rotational motor is a stepper motor, or the like, that is capable of extremely precise computer controlled movement. Based on programming provided through the electronic controllers 110 and the CPU 130 (such as through a user interface that allows a user to change certain parameters of operation of the electronic controllers 110 and therefore various components of the cutting assembly 140), the rotational motor can be programmed to cause the pulley 210 to rotate a specified number of degrees, so as to rotate the spindle 206 and feed motor 204 by the same specified number of degrees. Hence, the entire feed motor assembly 204 rotates, along with any gripped stock material 202 when the pulley 210 and spindle 206 are rotated by the rotational motor. Alternative embodiments could include different arrangements of the feed motor assembly 204 and the rotational motor, such as a feed motor assembly that only moves the stock material 202 along the X-axis and a rotational motor that grips and turns the stock material 202 when it is not being fed along the X-axis.

In order to better illustrate the relationship between the various components of the cutting assembly 140, the stock material 202 is shown exiting the feed motor assembly 204 supported by an elongated feed trough 212, which extends from the feed motor assembly 204 to one side of the cutting area (where the stock material 202 is cut by the blades 214, as further described below), and then extends from the other side of the cutting area to an output area 216. In reality, the length of the feed trough 212 between the feed motor assembly 204 and the cutting area would be relatively short. This enables the feed motor assembly 204 to be much closer to the cutting area, such that the stock material 202 would be cut almost immediately upon exiting the feed motor assembly 204. Keeping the length of the stock material 202 short between the feed motor assembly 204 and the cutting area helps to better control the stock material 202 while it is being cut, i.e., preventing the stock material 202 from moving along the Y-axis (shown in FIGS. 2A and 2B as axis 242), the direction perpendicular to the spindle 206, or rotating while the stock material 202 is being cut.

It should also be noted that most of the stock material 202 is likely to be substantially rounded in shape, although other shapes could also be used. The stock material 202 has both width and height, giving it a Y-axis and Z-axis (shown in FIG. 2B as axis 244) position, where the Z-axis is vertical to a plane including the X-axis and Y-axis. The feed trough 212 is intended to passively guide the stock material 202 as it is moved along the x-axis, which it could do in many different ways, such as through the utilization of precisely located guide posts or elongated members or a guide path that maintains the stock material 202 in a desired position relative to the Y-axis and Z-axis. The guide path of the feed trough 212 for rounded stock material 202 is preferably V-shaped, as illustrated by the cross section shown in FIG. 2B, wherein the stock material 202 lies in the bottom of the point formed by the V-shaped guide path within the feed trough 212.

As noted above, the cutting area is defined by a small gap between the two sections (prior to and after the cutting area) of the feed trough 212 where a pair of opposing blades 214 cut the stock material 202. In an embodiment of the application, the two blades 214 can be either semiconductor dicing blades or standard "tooth" type blades formed of a carbide material, such as tungsten carbide, to improve wear resistance. The submicron grain size of tungsten carbide and similar composites works well because they are less brittle, extremely hard, and can maintain their sharpness even at very small blade thicknesses. In an embodiment, additional different types of cutting instruments and systems could be utilized in place of the blades 214, such as water jet cutting systems, flame or oxyfuel cutting systems, plasma (arc) cutting system, electric discharge machining (EDM), etc., although not all of these systems are appropriate for use when cutting non-metal stock material or even certain types of metal stock materials, such as softer metals and less conductive metals. Given the variable operation of such additional types of cutting systems, it may also be necessary and/or desirable to change the orientation of the cutting assembly 140 and/or the stock materials 202 so instead of bringing the cutting point of the blade or system down along the Z-axis, the cutting point may be moved in the X-axis, or the cutting point may be held stationary while the stock materials is moved relative to the cutting point. All such alternative cutting systems are anticipated herein. Hence, when reference is made herein to a "dual blade" system, it is to be understood that any type of alternative cutting member or cutting system could also be used, depending on the application involved.

An embodiment for cutting plastic utilizes a tooth type blade with approximately 56 teeth. When cutting PEEK (polyetheretherketone) and other plastics with this blade type, a blade thickness of approximately 0.006 and 0.008 inches works well. When cutting nitinol, stainless steel and other hard metal and composite materials, a diamond semiconductor dicing blade with a thickness of approximately 0.002 inches works well. Given such thickness, the size of the open cutting area between the two sections of feed trough 212 represented in FIG. 2A is not to scale and is exaggerated in size in order to more clearly illustrate the opening of the cutting area. Of course, the blades 214 shown in FIG. 2A appear to be much larger in diameter than they really are as well, especially since, in most cases, they are only required to make very shallow cuts in the stock material 202. Since the stock material 202 could be formed of any type of material having any size diameter, such larger stock material would obviously need to be cut with thicker blades having larger diameters than those used to cut guidewires and catheters.

As will be further noted below, the embodiment does not require the stock material 202 to be of a metallic composition so its location can be electromagnetically sensed by the blades 214 before a cut can be made. The embodiment can be used to cut any type of material, whether metallic or non-metallic, such as PEEK, a semi-crystalline, high temperature thermoplastic that is ideal for use in catheters due its high modulus of elasticity resulting in torqueability and the ability to hold a shape. Although the general belief in the art has been that lower cutting speeds were necessary, especially when cutting PEEK, to reduce spur generation in the area of each cut, this was found not to be the case; much higher rotational speeds of the blades 214 worked well to reduce spur generation and provide exception accuracy. The embodiment also cuts other materials, including stainless steel and metallic composites at very high speeds with no burrs and with exceptional accuracy.

The blades 214 are located within a blade enclosure 218 (shown without its top in FIG. 2A so the interior can be viewed) through which air can be pumped to cool the blades 214 and the stock material 202, and through which debris cut from the stock material 202 can be removed. The hoses 220 of the air handling system can be used for pumping air and/or vacuuming air from the blade enclosure 218. The blades 214 can also be water cooled, as is known in the art.

In order to drive the blades 214 directly at higher speeds without requiring more expensive motors and added additional complications, each of the blades 214 is attached to a spindle 222, that is oriented parallel to the X-axis. Each of the spindles 222 is driven by a belt 224 that is rotated by a pulley attached to the spindle motor 226. The spindle motor 226 is program controlled through the electronic controllers 110 and the CPU 130. The blades 214 are driven indirectly in this manner so as to achieve greater rotational speeds than would be possible or practical with a direct drive arrangement. For example, the spindle motor 226 is capable of running at approximately 4,000 revolutions per minute (rpm) over an extended period of time without stressing the spindle motor 226 or any of the bearings supporting the pulley. The aspect ratio between the pulley and the spindle 222 is approximately 6:1, so the slower rotating spindle motor 226 is capable of rotating the spindle at approximately 24,000 rpm, the desired speed for cutting PEEK and other materials. A direct drive motor capable of operating at 24,000 rpm would be significantly more expensive, require different bearing assemblies, and likely have a significantly higher failure rate.

The combination of the blade 214, the spindle 222, the spindle motor 226 and pulley, and the belt 224 is referred to herein as a "cutting assembly", but the same term would apply if a different cutting system without blades was being used as well. Each cutting assembly is attached to a blade stepper motor 228 that controls the Y-axis location of each blade 214. The stepper motors 228 are mounted on a movable frame assembly 230, as further described below. Each of the stepper motors 228 are program controlled through the electronic controllers 110 and the CPU 130, or can be manually adjusted through the control knobs 232.

To cut a piece of stock material 202 so as to leave a resultant beam, as further described below, of a specified dimension, each of the stepper motors 228 are adjusted to a predetermined location such that the blades 214 are close but not touching, and a cut is made in the uncut stock material 202 with both blades at the same time. The manner in which both blades cut the stock material 202 simultaneously is further described below. Once the cuts are made, the resultant beam is measured to determine if it is of the desired dimension. The stepper motors 228 are then adjusted along the Y-axis to move the cutting assemblies inward toward each other or outward away from each other, and another cut is made to the uncut stock material 202. This process is continued until the desired resultant beam dimension is achieved, at which point a series of cuts in the uncut stock material 202 is carried out.

By mounting the cutting assemblies on the stepper motors 228, it is possible to precisely control the Y-axis location of each blade 214 and to accommodate a larger variety of different stock materials 202, such as raw wire, tubing, and other shapes and sizes of cylindrical stock materials 202. For example, if a wide diameter catheter is to be cut from a relatively wide diameter piece of tubing, the stepper motors 228 can move the cutting assemblies apart to accommodate the larger than normal stock material. In another example, it may be that a user wishes to micro-cut a piece of metal wire for a guidewire having 0.002 inch resultant beams at one end and 0.004 inch resultant beams at the opposite end, with a gradual transition between the two beam widths. In this example, the stepper motors 228 can be precisely controlled by electronic controllers 110 and processor 130 to position the blades 214 to make cuts resulting in the desired resultant beam width, whether that be 0.002 inches, 0.0025 inches, 0.003 inches, 0.004 inches, etc. Thus, almost any desired dimension can be machined at any specified location.

Both of the cutting assemblies and the stepper motors 228 are in turn mounted on the movable frame assembly 230, which is moved up and down along the Z-axis by a Z-axis motor (not shown) located within the movable frame assembly 230 and mounted on a non-visible portion of the stationary frame assembly 200. By mounting the cutting assemblies and stepper motors 228 on the movable frame assembly 230, it is possible to precisely control the Z-axis position of both blades 214 at the same time. The blade enclosure 218 can be designed to be mounted to the movable frame assembly 230, such that the blade enclosure 218 moves along with the blades 214, or blade enclosure 218 could include two slots within which the spindles 222 could move up and down apart from the blade enclosure 218. So as to better seal the interior of the blade enclosure, it is preferable to have the blade enclosure 218 move with the blades 214.

Also shown in FIG. 2A (by dotted lines so that underlying components are visible) is the imaging system of the embodiment, which primarily comprises a digital camera 234 mounted within an upper cowl 236 and upper and lower lights, not shown. The upper cowl 236 is mounted to the stationary frame assembly 200 so that the camera 234 does not move along the Z-axis as the blades 214 move. The camera 234 is positioned directly over the cutting area and is focused on a portion of the stock material 202 as it is being cut and just after it has been cut, as further illustrated in FIGS. 3 and 4.

The camera 234 could be any of a number of commercially available high-speed digital video cameras as long as it is capable of capturing high quality pixilated video image data. In an embodiment, the camera is a model AM-413T digital microscope camera, manufactured by SunriseDino of New Hyde Park, N.Y. The more interesting aspects of the imaging system are the manner in which the stock material 202 is backlit and illuminated in order to increase contrast around the edges of the cut stock material 202 and how the digital image processing is capable of precisely measuring both cuts and the resultant beams.

Figure 3:
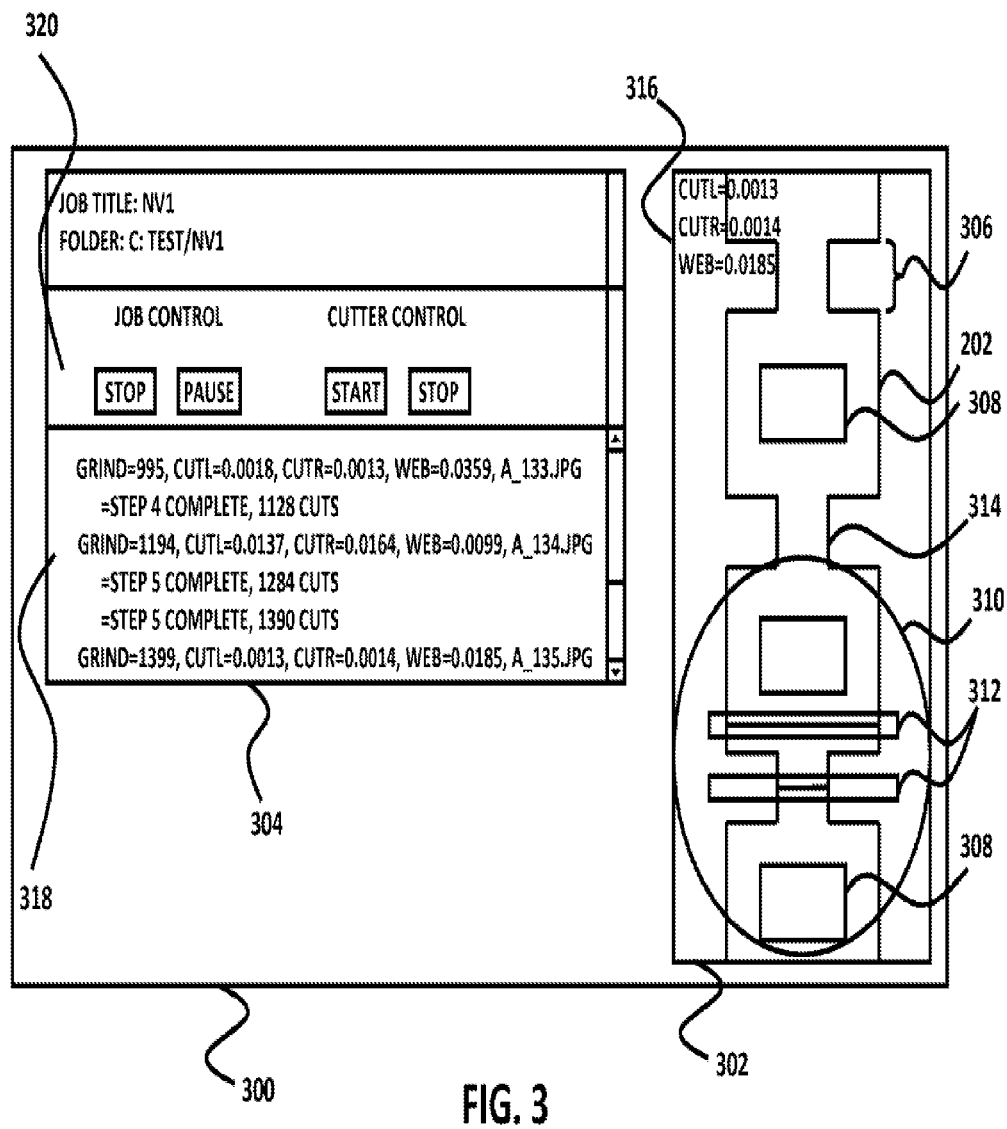
FIG. 3 illustrates a desktop image generated by the imaging system and CPU of FIG. 1 depicting the stock material once it has been cut by the cutting assembly.

FIG. 3 is an illustration of a desktop image 300 generated on the display of the CPU 130. The desktop image 300 includes an imaging window 302 and a control window 304. The imaging window 302 displays digital video images of the stock material 202 as it is being cut and as it is being measured by the imaging system. The area 306 shows the stock material 202 just after it has been cut by the blades 214 and the blades 214 have moved beyond the focused view of the camera 234. The stock material 202 being cut in the example illustrated in FIG. 3 is a tube used to make a catheter that is being rotated ninety degrees) (90.degree.) after each cut. Once a cut has been made, holes 308 are formed in the walls of the stock material 202 that become visible as the stock material 202 is turned in order to make the next cut. As the stock material 202 advances along the X-axis of the cutting assembly, the stock material 202 passes in front of a backlight, illustrated by the circle 310.

Figure 4:
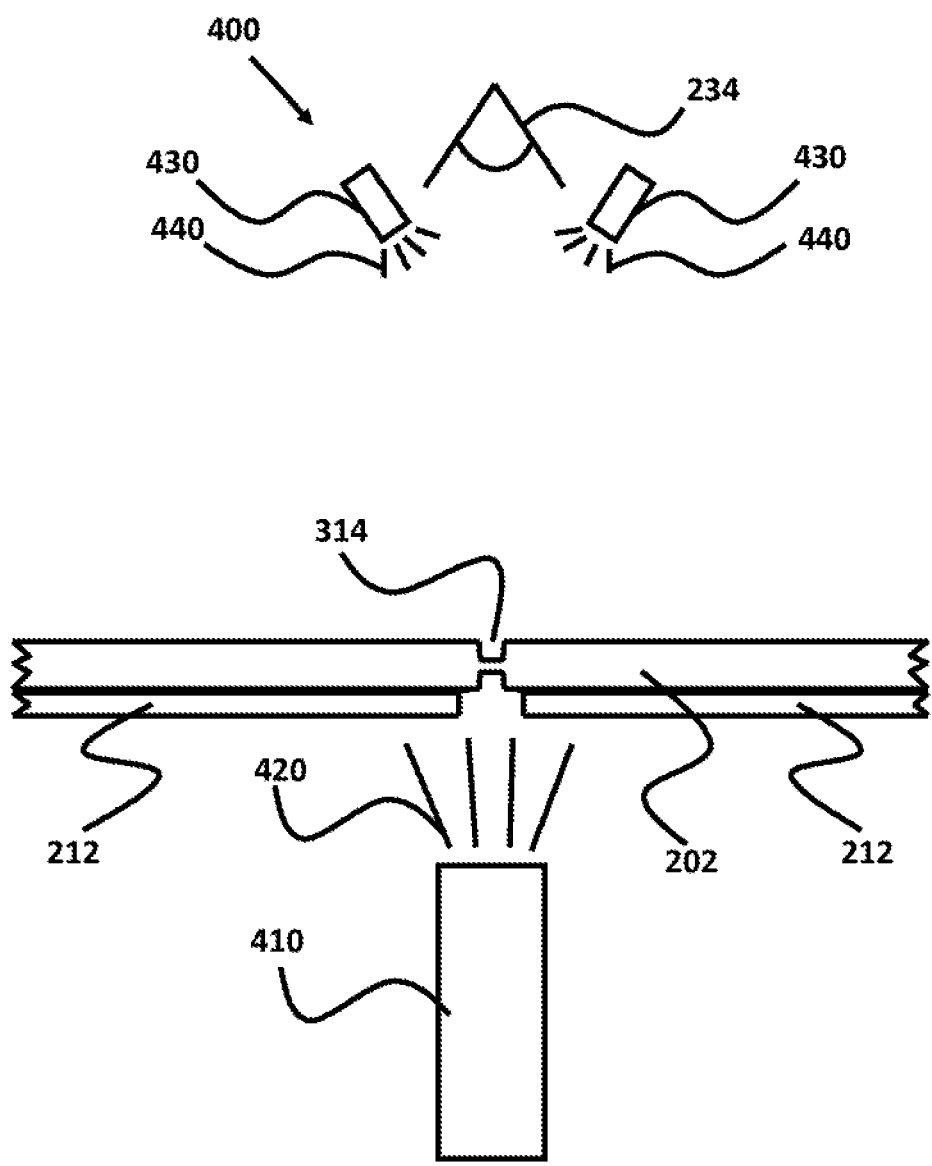
FIG. 4 illustrates the imaging system of the cutting assembly of FIG. 1.

Referring briefly now to FIG. 4, the camera 234 of the imaging system 400 is placed directly over the top of stock material 202, so that it may image and measure the stock material 202 and the resultant beam 314 formed by the two cuts. As discussed above, feed trough 212 leaves a gap through which the blades 214 can pass. The backlight 410 is an optical fiber, or a bundle of several optical fibers, through which red LED light 420 is provided by the imaging system. The optical fiber providing the backlight 410 is passed through a separately drilled hole (not shown) that enables the backlight 410 to shine around the stock material 202 and be visible to the camera 234. The backlight 410 is held in place below the cutting area by an anvil that is affixed to the stationary frame assembly 200 and is positioned to illuminate the stock material 202 just after it has been cut, although the stock material 202 can also be seen in imaging window 302 just as it is being cut. Camera 234 is communicatively coupled to processor 130 (not shown in FIG. 4) in order to provide feedback while the stock material 202 is being cut, and in order to store one or more images of one or more resultant beams 314.

A set of one or more green and blue LEDs 430 can be positioned above the stock material 202 and around the camera 234 to provide additional lighting 440 for a user to see the top side of the stock material for manual inspection purposes. The combination of a red backlight 410 and the green and blue LEDs 430 was selected because the camera 234 provides three color image channels of image data (red, green and blue) and the separately colored lighting enables the image data to be easily separated. The CPU 130 (and the software it operates) receiving the image data uses the red image channel for edge detection because it provides a high-contrast back lit image of the cut with no front side reflections that would confuse the measurement software being utilized by the CPU 130 to measure each cut. The green and blue image data created by the green and blue LEDs 430 and the camera 234 are transmitted through the green image channel and the blue image channel, respectively.

A purpose of the imaging system 400 is to monitor the exact location and size of cuts formed in the stock material 202. This information, meaning the image of a cut and resultant measurements, can be used in a number of different ways. For example, the images can be used to validate the accuracy and repeatability of the micro-cutting machine at or near in time to when the stock material 202 is being cut. If the images are being analyzed on the fly—while in the process of making the many cuts necessary to transform a piece of stock material 202 into a catheter or guidewire—the imaging system 400 can be used to stop production on that piece if a cut goes awry or the stock material 202 is out of tolerance.

Returning now to FIG. 3, although the camera 234 could theoretically capture an image of every single cut made to the stock material 202, doing so would generate an excessive amount of data that could not be competently reviewed at a reasonable cost by human operators. Instead, so as to provide adequate quality control, images are captured and recorded on a periodic or random (randomized test sampling protocol) basis, as further described below. While an image of the stock material 202 is being captured, as illustrated in FIG. 3, two visual overlays 312 are applied by the imaging system to the image data within the back lit area 310 to determine the length of each cut and the resultant beam 314, which is referred to as the "web" in FIG. 3. The overlays 312 measure across the stock material 202 at two or more different points, including at least the width or thickness of the stock material 202 and the width of the web or resultant beam 308.

The measurements taken by the overlays 312 are then analyzed by the CPU 130 and utilized to determine the length of the left cut, the right cut and the resultant beam or web 314. For example, by pre-determining the number of pixels per unit of measurement in the image being captured, and then counting the number of pixels displayed in the image data for the length of an object to be measured (using real-time image processing software operated by the CPU 130), it is possible to determine accurate measurements from the image data alone, without having to make use of mechanical measuring means. For example, if it is known that a piece of stock material 202 to be cut should have a width of 0.039 inches and the image data has a pixilation of 500 pixels per 0.05 inches, then approximately 390 pixels correspond to the width of the stock material 202. If a cut is then made in the stock material 202 from both sides leaving the resultant beam 314, and that resultant beam 314 is measured at 359 pixels, then the resultant beam 314 has a width of 0.0359 inches. Similar measurements can be made of each cut in the stock material 202 and these real-time measurements can then be displayed at 316 so the progress of the cutting operation can be monitored by an operator or the CPU 130.

When the width of the stock material 202 at the point of a cut is thicker or thinner than expected, the resultant beam 314 will still be within an acceptable range of its normal size because the position of the blades 214 relative to the stock material 202 is largely based on the centered position of the stock material 202, versus the known technique of basing each cut on the relative difference of the separate blades to the side of the stock material each blade is responsible for cutting. Hence, when thicker stock material 202 is cut, more stock material is cut away and when thinner stock material 202 is cut, less stock material is cut away, but in each case leaving a resultant beam of the desired size, versus generating thicker or thinner desired resultant beams, as is common in the art.

The control window 304 displays each measurement in a log section 318 of the control window that can be scrolled. As illustrated in FIG. 3, the CPU 130 has been programmed to instruct the imaging system to capture an image and measure the left cut, the right cut and the web on a periodic basis. For example, the first cut shown was grind 995 that resulted in a left cut (CUTL) of 0.0018 inches, a right cut (CUTR) of 0.0013 inches, and resulted in a web of 0.0359 inches, as noted above. The measurements and image file for grind 995 is then stored in a data file labeled A.sub.—133.JPG. The grinds being recorded do not necessarily correspond to the same number of cuts that have been made, as more or less cuts may be made than are imaged, measured and recorded. Hence the steps illustrated as part of the log section 318 may correspond to a separate programmed process that keeps track of the number of cuts that have been made.

The control window 304 also includes selectable buttons 320 that allow an operator to stop or pause a job or start and stop the cutting process. The operator also has the option of assigning a title to each cutting job and to store the data associated with that cutting job in a particular folder on the CPU 130.

As previously noted, the CPU 130 provides programmed control of the electronic controllers 110, the rotational motor and the feed motor assembly 204 to control the movement of the feed stock 202 into the cutting assembly 140 along the X-axis. Once the stock material 202 has been fed into the cutting assembly and gripped by the feed motor assembly 204, the CPU 130 would instruct the rotational motor either to leave the stock material 202 at its current orientation or to rotate it by some degree specified by the CPU 130. Once the stock material 202 has been cut, the feed motor assembly 204 would advance the stock material 202 by some specified amount along the X-axis to position it for the next cut and grip the stock material 202. The rotational motor would then rotate the feed motor assembly 204 and the stock material 202 would be cut again. This process would then be repeated until all of the stock material 202 has been cut as desired.

By rotating the stock material 202 between each cut, the cutting assembly 140 can generate a cut stock material 202 with resultant beams 314 that are not all aligned in the same orientation along the length of the micro-machined product. For example, the stock material 202 could be turned ninety degrees from its angle at the time of the last cut, or many variations thereof, such as turned five or more degrees short of ninety degrees (i.e., 85 degrees) from the angle of the last cut, or even cut at random angles relative to the angle of the last cut.

An additional feature of the embodiment is the ability to measure the stock material 202 prior to being cut and using the resultant measurement to guide the depth of cuts. If stock material 202 was assumed to be 0.039 inches in diameter and it was desired to create a resultant beam 314 having a thickness of about 0.008 inches, then each cut would need to be 0.0155 inches deep. If the imaging system determined that the stock material 202 was only 0.032 inches in diameter instead of 0.039 inches, then the cutting machine would know that it needed to reduce the depth of each cut to 0.012 inches so as to leave the desired resultant beam 314 of 0.008 inches. However, as noted above, this is not necessary with respect to the embodiment where two blades 214 cut down from opposite sides of the stock material 202 because once the relative gap between the blades 214 has been established (that is relative to the cutting points of the two blades 214 or other cutting members), the gap dictates precisely the resultant beam 314 regardless of the outside diameter of the stock material 202. While the amount of material, or "depth of cut" is indeed different, there is no difference in the resultant beam 314 width.

In certain cases, however, it may be desirable to operate the blades 214 in an "offset cut" mode, wherein the blades 214 are not aligned in the same plane and deeper cuts are made. In this case, the cuts appear as independent cuts from each side (although cut simultaneously). The depth would then be important as each resultant beam, and the flexibility and stability of this type of structure, would be determined by the distance from the end of the cut to the opposing side of the tube. Although this type of structure could be made using the embodiment, it may not be terribly practical since it would require the cutting machine to image and measure the stock material 202 before each cut was made and to adjust the stepper motors 228 on the fly in the event it was determined that the stock material 202 was of the wrong diameter in order to change the depth by which the cuts are made.

Accordingly, the embodiment presently relies upon a quality control technique that measures only some of the cuts after they have been made instead of every cut. This enables the system to monitor the quality of the stock material 202 and other aspects of the system, but does not necessitate changing how the system is operating from cut to cut. For example, in the event stock material 202 was out of specification, it is not likely that its diameter would only vary at a single isolated point. Rather, if stock material 202 was out of specification at one point, it would likely be out of specification along of a length of the material or be out of specification at multiple individual points, one or more of which would be detected through the quality control technique. Large variations in the diameter of the stock material 202 may make the stock material undesirable for certain applications, so if this was determined, the cutting assembly 140 could be stopped and the product discarded once detected.

As stated, a main purpose of the micro-cutting machine is to make pairs of cuts (but not necessarily opposing) on cylindrical stock material to form flexible and torquable products, such as guidewires, catheters and other similar types of devices, all referred to herein as "products". While it is known in the art to create a flexible and torquable guidewire and catheter by making a single cut with a blade into a side of a cylindrical piece of stock material (metal wire and/or tubing), and then rotating the material and making an opposing cut on the opposite side of the stock material with the same blade. When this process is performed along all or part of the length of the stock material, the diameter of the stock material is reduced in numerous places, which increases the flexibility of the resulting product, but since the product retains the same overall outside diameter, the resulting product is able to retain much of its torquability. While the stock material cut in this fashion is usually cylindrical, since the cuts are made from opposing sides or nearly opposing sides toward the middle, it is helpful to think of the stock material as having a first side and a second side, even though in reality the stock material is substantially round and has only a single side.

Figure 5C:
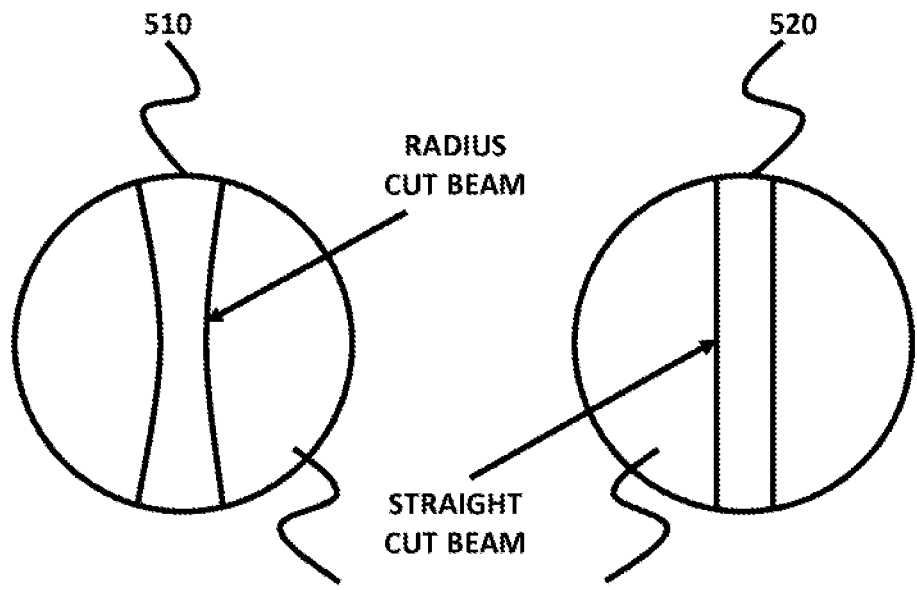
Figure 5C:
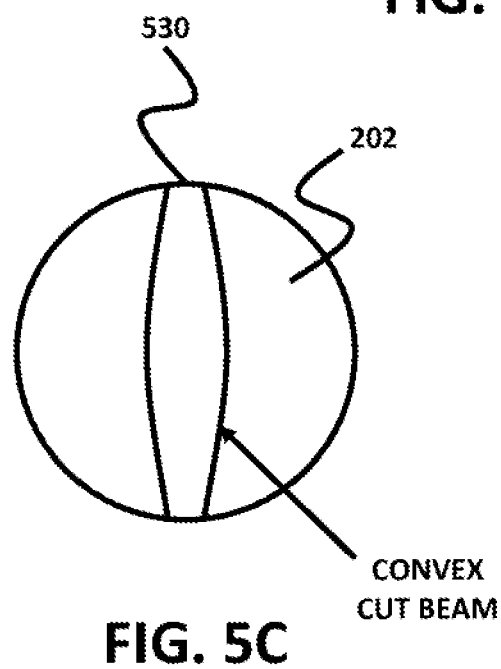

FIG. 5A illustrates the resulting beams that are generated by circular blades that cut from a first side and then a second side, a resulting beam that can also be generated through utilization of the embodiment. FIGS. 5B and 5C illustrate resulting beams that can only be generated through utilization of the embodiment. A cross-sectional view of solid stock material 202 is shown in FIGS. 5A, 5B and 5C. Based on existing technology, when the solid stock material 202 has been cut on the first and second sides (either all at once, as is presently disclosed, or on the first side and then on the second side, as is known in the art), a resultant beam 510 would remain. This type of resultant beam 510 is known in the art as a radius cut beam because it tapers from the circumference to the center point. Existing technology cuts the solid stock material 202 by advancing toward the solid stock material 202 along the Y-axis described above. As a result, the circular blade cuts the stock material 202 further in the central area than it can on the outer areas, always resulting in the radius cut beam 510.

Although a radius cut beam 510 is appropriate for some uses, it is not ideal from a torquability and safety perspective. The reduced thickness of the central area of the radius cut beam 510 enables stress to build up in that area as the product is twisted, which can result in breakage of the product. Given that products are often used in intravascular procedures, any breakage is highly undesirable. Likewise, if there is any irregularity in the diameter of the product, which irregularity cannot be sensed by the cutting machine, the cutting machine will make a cut in the product based on its programming alone. Hence, using the example provided above, if a guidewire was 0.039 inches in diameter and it was desired to create a resultant beam having a thickness of about 0.008 inches at the central area, then each cut would need to be 0.0155 inches deep. If the guidewire, however, was only 0.032 inches in diameter and the cutting machine used electromagnetic sensing, instead of real-time imaging, then each side would still be cut by 0.0155 inches, leaving a resultant beam of 0.001 inches, which would also likely result in breakage when inserted into a simple curve.

The presently disclosed cutting machine, however, operates by moving the dual blades 214 along both the Y-axis and the Z-axis and is capable of creating a variety of differently shaped resultant beams, including the radius cut beam of FIG. 5A, as well as the straight cut beam of FIG. 5B and the convex cut beam of FIG. 5C. To create the straight cut beam, the cutting assemblies are moved above the stock material 202 along the Z-axis and adjusted along the Y-axis to create a distance between the blades, or other cutting member being used, sufficient to create a resultant beam of a desired thickness, then the cutting assemblies are brought down along the Z-axis and across the stock material 202. Hence, the machine is able to produce straight cut resultant beams, like resultant beam 520. A straight cut resultant beam 520 will enable greater and more consistent flexibility, due to the linear shape of the resultant beam, while retaining at least the same torquability as the radius cut beam, without the increased possibility of breakage.

To adjust the relative gap distance (or the resultant beam) between the blades or cutting members, a cut can be made, the resultant beam measured, and the cutting assemblies can be further adjusted along the Y-axis until a resultant beam of the desired width has been created. Alternatively, a reference stock of a known width can be placed between the blades/cutting members until both blades/members touch the reference stock.

As noted, a radius cut beam 510 or a convex cut beam 530 could be created by the herein disclosed micro-cutting machine by moving the cutting assemblies inward and outward along the Y-axis as each cut is being made. It would also be possible to make a variety of other types of cuts and resultant beams by varying combinations of elements at the same time, such as rotating the stock material 202 with the rotation motor as a cut is being made, or rotating the stock material 202 and moving the cutting assemblies along the Y-axis at the same time. For example, a spiral cut could be made by leaving the cutting assemblies at a set Y-axis position while the stock material 202 is rotated by the rotational motor. As these types of cuts have not been possible before, the advantages of the different cuts is not yet fully known, but it can already be anticipated that a convex cut beam 530 would have even better flexibility and torquability properties than either the straight cut beam 520 or the radius cut beam 510.

As previously noted, the automated feedback and control process carried out by the imaging system 400 and the processor 130 can account for slight variances in cutting blade variations or in variations or imperfections of the stock material itself. The resultant beam, as discussed above, is the critical dimension and could be affected by even a single blade variation (such as a single blade tooth being too long) or by a variation of the diameter of the stock material throughout its length. All these factors are of course integrated into and manifest themselves in the resultant beam dimension. The precise measurement and adjustment capabilities of the embodiment result in unprecedented precision. Upon measurement of the resultant beam, the centering of the resultant beam with respect to the located stock surfaces, and the alignment of the two cuts to each other, the processor 130 can make adjustments to bring all parameters into alignment to create precise resultant beam widths. This process can be executed at the beginning of manufacture, as a set-up process, as one or more cuts are being made, as a periodic check, or as each and every cut is being made. The software run on processor 130 can be used to validate the repeatability of the micro-cutting machine, possibly reducing the number of measurements necessary while cutting a piece, or rendering continuous measurements unnecessary.

The micro-cutting machine of the embodiment, as previously noted, is capable of micro-cutting a wide variety of stock materials. Traditional single-blade micro-cutting machines make use of electromagnetic sensing of the precise location of the stock material relative to the single blade, thereby requiring the use of stock material that is conductive. This condition rules out the use of plastic tubing stock material or any other non-conductive or minimally conductive material (referred to herein as "non-conductive" even if the material has some relatively low conductivity that is insufficient to be cut by prior machines).

As discussed, the high definition images and measuring capabilities of the imaging system and the precise positioning of the cutting assemblies of the embodiment are much more accurate than relying upon sensing a surface of the stock material because the stock material itself can have an imperfect or inconsistent diameter. Therefore, the herein disclosed micro-cutting machine is much more accurate and can therefore cut finer dimension resultant beams with greater reliability. The physical arrangement of the components of the cutting assembly 140 and the stock material 202 make it possible to cut harder materials with less natural flexibility, like stainless steel, because the resultant beams can be cut very narrow while retaining precision. The dual blade micro-cutting machine of the embodiment is therefore fully capable of cutting stainless steel catheters and guidewires (greatly desired by surgeons for its ability to hold a shape—allowing the surgeon to personally shape the tip of a stainless steel guidewire to match the patient's endovascular system just prior to use), plastic catheters and guidewires (desirable for their great flexibility at relatively wider diameters), and other non-magnetic stock materials for all types of products.

Flexible yet torquable products are formed by repeating micro-cuts throughout either the entire length of a piece of stock material, or along one or more portions of the piece of stock material. Ideally, the pairs of cuts (a pair of cuts refers to one pass by the dual blades even though the cuts may not be opposite) are ideally made in a rotating pattern along the longitudinal axis of the cylindrical stock material. A rotating pattern is preferred because making all cuts at the same angle creates a product that is biased toward flexing in one direction—perpendicular to the resultant beam. If the stock material is rotated about its longitudinal axis between a prior cut and a next cut or a prior pair of cuts and a next pair of cuts, then the resultant beams are not all aligned in the same plane and the flexing bias is lessened or eliminated. This rotation between cuts is facilitated by feed motor 210 and the rotational motor, illustrated in FIG. 2. Feed motor 210 grips the stock material 202 as the rotational motor rotates the stock material 202 along the X-axis (the longitudinal axis of the stock material 202), according to directions received by electronic controllers 110 and determined by processor 130. The rotation between pairs of cuts is referred to as a variance, and is measured in the degree of rotation about the longitudinal axis of the stock material.

Figure 6A:
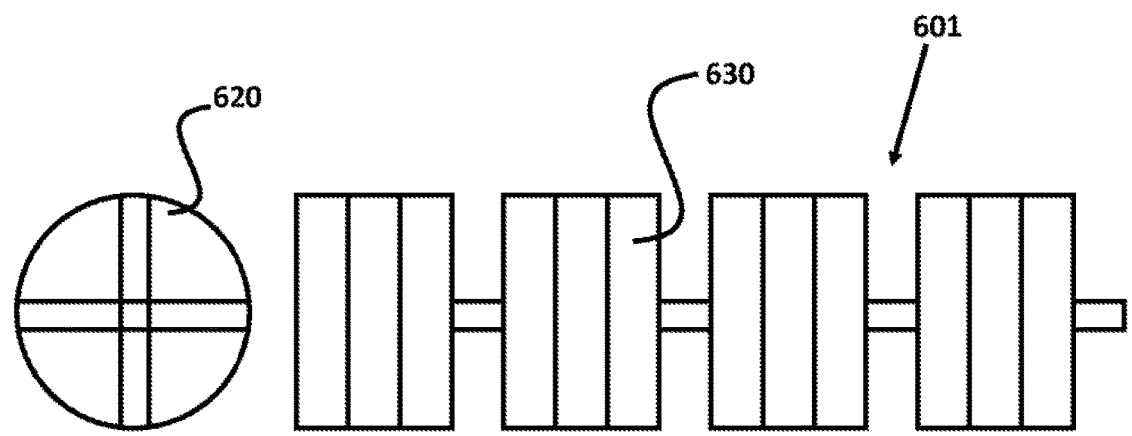
FIGS. 6A and 6B illustrate cross-sectional views of pieces of cylindrical stock material cut to form different products in accordance with an embodiment.
Figure 6B:
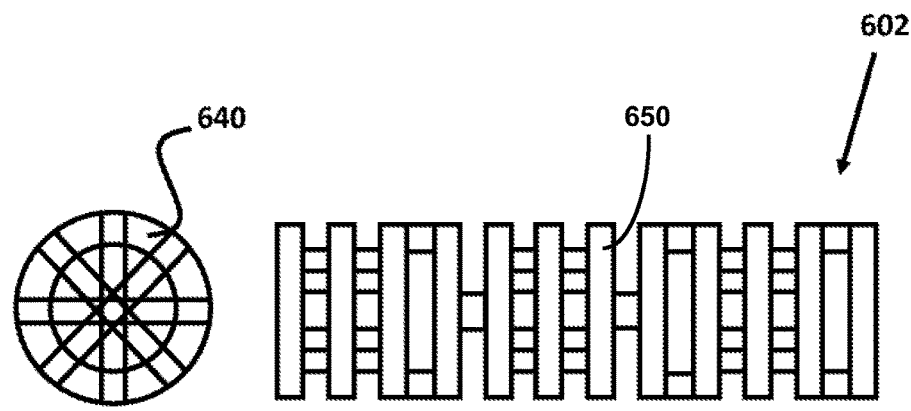

FIGS. 6A and 6B illustrate two examples of a rotating pattern of pairs of cuts and resultant beams. FIG. 6A illustrates a ninety degree variance guidewire 601 that was micro-cut using the dual blade micro-cutting machine of the embodiment. Cross-sectional view 620 illustrates the two different angles at which pairs of cuts are made when the stock material is rotated ninety degrees between cuts. Plane view 630 illustrates how such a guidewire 601 appears along its length. FIG. 6B illustrates a forty-five degree variance guidewire 602 that was micro-cut using the dual blade micro-cutting machine of the embodiment. Cross-sectional view 640 illustrates the four angles at which pairs of cuts are made when the stock material is rotated forty-five degrees between cuts. Plane view 650 illustrates how such a guidewire 602 appears along its length.

A ninety degree variance, as illustrated by guidewire 601 in FIG. 6A, is significantly better than aligning all resultant beams in the same plane, but is still not ideal. The ninety degree variance results in resultant beams that are perfectly perpendicular to each other, which may cause the overall guidewire to be biased toward flexing in two directions—upward and downward, and to the left and to the right, if the guidewire is aligned like guidewire 601 in FIG. 6A. Using a forty-five degree variance between cuts, like guidewire 602 in FIG. 6B, can improve the flexing situation, because the resultant beams are now no longer oppositely aligned in only two planes. This form of cuts evens out the guidewire's flexing properties so that it is not biased in two distinct directions. In fact, an exemplary embodiment may utilize an uneven variance between cuts, such as ninety-five degrees, or forty degrees, so that the pairs of cuts, and therefore the resultant beams, truly spiral around the longitudinal axis—completely eliminating flexing bias in any one direction. Of course, the variance used in cutting a product can be even more complex. For example, advantageous results can be achieved by using a ninety degree variance between a first cut and a second cut, and then rotating the stock material slightly, such as by five degrees, before making a third cut and a fourth cut, the third cut and the fourth cut again using a ninety degree variance.

An additional feature of the dual blade micro-cutting machine of the embodiment is an ability to cut a serial number using the blades 234 or cutting member as controlled by the cutting assembly 140, electronic controllers 110 and CPU 130 into the stock material 202, so that the final product can be individually identified. The serial number or other form of identification could be formed by creating a series of cuts in the stock material 202 (possibly circumferentially so they can be read regardless of the rotation of the stock material 202) of varying width and/or varying spacing that could be read in a manner similar to a bar code.

Finally, it should be noted that while throughout the specification the micro-cutting machine has been described as utilizing a pair of cutting blades cutting simultaneously, it also may be possible to configure a micro-cutting machine utilizing two or more pairs of cutting blades or members operating concurrently. In this way, it may be possible to operate a plurality of resultant beams all at one time. In such a configuration, the pairs of cutting members would all be communicatively connected to electronic controllers 110 and processor 130, so that they can each be adjusted in unison to machine a product meeting the desired resultant beam parameters.

While embodiments have been illustrated and described herein, it is to be understood that the techniques described herein can have a multitude of additional uses and applications. Accordingly, the invention should not be limited to just the particular description and various drawing figures contained in this specification that merely illustrate one or more embodiments and application of the principles of the invention.

What is claimed is:

1. A micro-cutting system for forming cuts along a length of a catheter or guidewire stock material to form a catheter or guidewire product, the system comprising:
    a cutting apparatus configured to form a plurality of pairs of grooves substantially perpendicular to a longitudinal axis of the stock material, the cutting apparatus including:
    a first cutting blade having a cutting edge aligned to be substantially parallel to a vertical axis;
    a second cutting blade having a cutting edge aligned to be substantially parallel to the vertical axis; and
    one or more motors operably coupled to the first and second cutting blades, the one or more motors configured to move the first and second cutting blades in a direction substantially perpendicular to the longitudinal axis of the stock material to bring the first and second cutting blades into contact with the stock material to cut the stock material and form each pair of grooves, the one or more motors also being configured to control a relative gap distance between the first and second cutting blades along a lateral axis,
    wherein each pair of grooves extend in a direction substantially parallel to the vertical axis as a result of the one or more motors moving the first and second cutting members in a direction substantially perpendicular to the longitudinal axis of the stock material, and
    wherein each pair of grooves are separated along the lateral axis so as to leave a resultant beam between the grooves of each pair of grooves formed in the stock material; and
    a stock material controller configured to hold the stock material and feed the stock material along the longitudinal axis through the cutting apparatus to enable the formation of successive pairs of grooves along the longitudinal axis of the stock material, the stock material controller being further configured to selectively rotate the stock material by one or more predetermined angles around the longitudinal axis between cuts to form one or more rotated offsets between cuts.

2. The system of claim 1, wherein at least one of said first cutting blade or said second cutting blade has a thickness between about 0.002 inches and about 0.008 inches.

3. The system of claim 1, wherein the cutting apparatus is configured such that the resultant beam is a radius cut beam, a straight cut beam, a convex cut beam, or a spiral cut beam.

4. The system of claim 1, wherein at least one of said one or more predetermined angles is between about 5 degrees and about 90 degrees.

5. The system of claim 1, wherein at least one of said one or more predetermined angles is between about 5 degrees and about 45 degrees.

6. The system of claim 1, wherein said stock material controller includes a rotational motor that selectively rotates the stock material by said one or more predetermined angles around the longitudinal axis.

7. The system of claim 6, wherein said rotational motor rotates the stock material at predetermined speed around the longitudinal axis as said first cutting blade and said second cutting blade simultaneously form each pair of grooves.

8. The system of claim 1, wherein said stock material controller includes at least one feed motor configured to hold the stock material and feed the stock material forward along the longitudinal axis a predetermined distance.

9. The system of claim 8, wherein said at least one feed motor feeds the stock material forward along the longitudinal axis at a predetermined speed.

10. The system of claim 1, further comprising an electronic controller communicatively coupled to said cutting apparatus and said stock material controller, said electronic controller configured to control operation of said cutting apparatus and said stock material controller.

11. The system of claim 10, wherein said one or more predetermined angles is controlled by said electronic controller.

12. The system of claim 1, wherein said first cutting blade and said second cutting blade simultaneously cut the stock material to form each pair of grooves.

13. The system of claim 1, further comprising:
    an imaging system configured to collect image data of the stock material and the resultant beam after one or more of the plurality of pairs of grooves are made in the stock material and transmitting said image data; and
    a processor communicatively coupled to said imaging system configured to receive the image data from the imaging system and measure at least an uncut diameter of the stock material and a width of the resultant beam.

14. The system of claim 13, wherein said imaging system includes a camera positioned on a first side of an imaging area and one or more light sources positioned on a first side and on an opposite side of said imaging area, said one or more light sources illuminating the stock material and the resultant beam within said imaging area and said camera capturing said image data as the stock material and the resultant beam are illuminated.

15. The system of claim 14, wherein said one or more light sources back-light the stock material and the resultant beam within said imaging area to increase visual contrast at one or more edges of the stock material to enable a measurement of the uncut diameter and the width.

16. The system of claim 13, wherein said first cutting blade and said second cutting blade simultaneously cut the stock material to form each pair of grooves, wherein said imaging system captures an image for one or more of each pair of grooves on a periodic basis or a random basis, and said processor stores said image.

17. A micro-cutting system for forming cuts along a length of a catheter or guidewire stock material to form a catheter or guidewire product, the system comprising:
    a cutting apparatus configured to form a plurality of pairs of grooves substantially perpendicular to a longitudinal axis of the stock material, the cutting apparatus including:
    a first cutting blade having a cutting edge aligned to be substantially parallel to a vertical axis;

a second cutting blade having a cutting edge aligned to be substantially parallel to the vertical axis; and a first spindle motor operatively coupled to the first cutting blade for driving the first cutting blade;

a second spindle motor operatively coupled to the second cutting blade for driving the second cutting blade;

a first stepper motor configured to move the first cutting blade along a lateral axis substantially perpendicular to the longitudinal axis of the stock material;

a second stepper motor configured to move the second cutting blade along the lateral axis substantially perpendicular to the longitudinal axis of the stock material, the first and second stepper motors thereby controlling a relative gap distance between the first and second cutting blades along the lateral axis, wherein the first and second cutting blades are configured to move in a direction substantially perpendicular to the longitudinal axis of the stock material to contact the stock material and to cut the stock material and form each pair of grooves, wherein each pair of grooves extend in a direction substantially parallel to the vertical axis as a result of the one or more motors moving the first and second cutting members in a direction substantially perpendicular to the longitudinal axis of the stock material, and wherein each pair of grooves are separated along the lateral axis so as to leave a resultant beam between the grooves of each pair of grooves formed in the stock material; and a stock material controller configured to hold the stock material and feed the stock material along the longitudinal axis through the cutting apparatus to enable the formation of successive pairs of grooves along the longitudinal axis of the stock material, the stock material controller being further configured to selectively rotate the stock material by one or more predetermined angles around the longitudinal axis between cuts to form one or more rotated offsets between cuts.

18. The system of claim 17, wherein said first spindle motor and said second spindle motor control rotational speed of said first cutting blade and said second cutting blade.

19. A method of manufacturing a catheter or guidewire product using the micro-cutting system of claim 1, the method comprising:

moving a stock material to a first position along a longitudinal axis;

controlling a relative gap distance along the lateral axis between a first cutting blade and a second cutting blade;

moving said first cutting blade and said second cutting blade in a direction substantially parallel to the longitudinal axis to cut a first pair of grooves in the stock material, the first pair of grooves extending in a direction substantially parallel to a vertical axis as a result of the one or more motors moving the first and second cutting members in a direction substantially perpendicular to the longitudinal axis of the stock material, the first and second cutting blades leaving a first resultant beam in the stock material having a width approximately equal to said relative gap distance;

moving the stock material to a second position along the longitudinal axis;

rotating the stock material by a predetermined angle around the longitudinal axis; and moving said first cutting blade and said second cutting blade in a direction substantially parallel to the longitudinal axis to cut a second pair of grooves in the stock material leaving a second resultant beam in the stock material, wherein said first pair of grooves is offset from said second pair of grooves by said predetermined angle.

20. The method of claim 19, further comprising varying said relative gap distance between said first pair of grooves and said second pair of grooves.

* * * * *